US00PP31168P2

(12) United States Plant Patent
Hansen

(10) Patent No.: US PP31,168 P2
(45) Date of Patent: Dec. 3, 2019

(54) ***PHLOX* PLANT NAMED 'BEDAZZLED LAVENDER'**

(50) Latin Name: ***Phlox* hybrid**
Varietal Denomination: Bedazzled Lavender

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,919

(22) Filed: Feb. 1, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ..... A01H 5/02
See application file for complete search history.

*Primary Examiner* — Annette H Para

(57) ABSTRACT

A new and unique cultivar of Hybrid Spring *Phlox* named *Phlox* 'Bedazzled Lavender' multi-stemmed compact habit, slowly spread plant with bright, glossy-green, lanceolate leaves. Flowers are sweetly fragrant, with deeply notched petals of deep purplish-pink with two deep purple marks in center near-white eye beginning mid-April, continuing for about six weeks on branched peduncles. Foliage stays clean and resists mildew, especially suitable as a potted plant and for the landscape.

1 Drawing Sheet

Botanical classification: *Phlox* hybrid.
Variety denomination: 'Bedazzled Lavender'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Jul. 9, 2018 by Walters Gardens, Inc., who obtained the plant and all information relating thereto, from the inventor. No plants of *Phlox* 'Bedazzled Lavender' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Bedazzled Lavender' and will be referred to hereafter by its cultivar name, 'Bedazzled Lavender', or the "new plant". The new plant was hybridized at a wholesale perennial nursery in Zeeland, Mich. on Mar. 3, 2014 as cross between *Phlox subulata* 'Emerald Pink' (not patented) as the female parent times *Phlox bifida* 'Top Notch' (not patented) as the male parent. The new plant passed initial evaluation on the spring of 2016 and was assigned the breeder code 14-240-1 through the remaining evaluation process. 'Bedazzled Lavender' was first asexually propagated by stem cuttings in the greenhouses at the same nursery in Zeeland, Mich. in June of 2016. The unique characteristics of the new plant have been found to be reproducible and stable in successive generations of asexually propagated and the resultant plants have been found to be identical to the original selection.

BRIEF SUMMARY OF THE PLANT

*Phlox* 'Bedazzled Lavender' is unique from all other Hybrid Spring *Phlox* or other *Phlox* known to the inventor. The nearest comparison plants known to the inventor include: 'Running with Scissors' U.S. Plant Pat. No. 28,738, 'Violet Pinwheels' U.S. Plant Pat. No. 25,884, 'Pink Parasol' U.S. Plant Pat. No. 28,881 and the two copending cultivars 'Bedazzled Orchid' and 'Bedazzled Pink'. 'Running with Scissors' is taller in flower habit, the flower color is medium to light violet pink, and flowering is for a shorter period and the flower coverage is not as complete. 'Violet Pinwheels' the flower is a deeper violet hue and the petals have a smaller apical notch and the habit is more open and less rounded. 'Pink Parasol' has a lighter pink flower with a white eye from anthesis to flower drop, and the two purple striae are thin and indistinct. 'Bedazzled Orchid' is taller in flower habit and the flower is lavender-pink with subtle purple eye. 'Bedazzled Pink' has flowers of bright medium pink and a star-shaped eye of dark purple. The female parent, 'Emerald Pink' has shorter habit and more aggressive growth, flowers of medium pink about a week earlier, and the petal lobes are rounded and not deeply bifid. The male parent, *Phlox bifida* 'Top Notch' has pale lavender flower color with deeply cleft bifid petal lobes. 'Bedazzled Lavender' has foliage that is intermediate in both length and size to both parents.

*Phlox* 'Bedazzled Lavender' differs from and all other *phlox* known to the inventor in the following repeatedly observed traits in combination:

1. Plants of compact habit, slowly spreading by rooting stems, producing clean, glossy, bright-green, lanceolate leaves.

2. Multiple heavily-branched stems produce lightly branched panicles.
3. Flower beginning in mid-April and continuing for about six weeks completely covering plant at peak flowering.
4. Sweetly fragrant flowers with petals that begin deep purplish-pink and lighten to very pale purple.
5. Individual petals are deeply notched at tips with two deep purple marks in near-white center eye.

BRIEF DESCRIPTION OF THE DRAWINGS

The photographs of the new plant demonstrate the unique traits of *Phlox* 'Bedazzled Lavender' and the overall appearance of a three-year-old plant growing in a full-sun trial bed in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
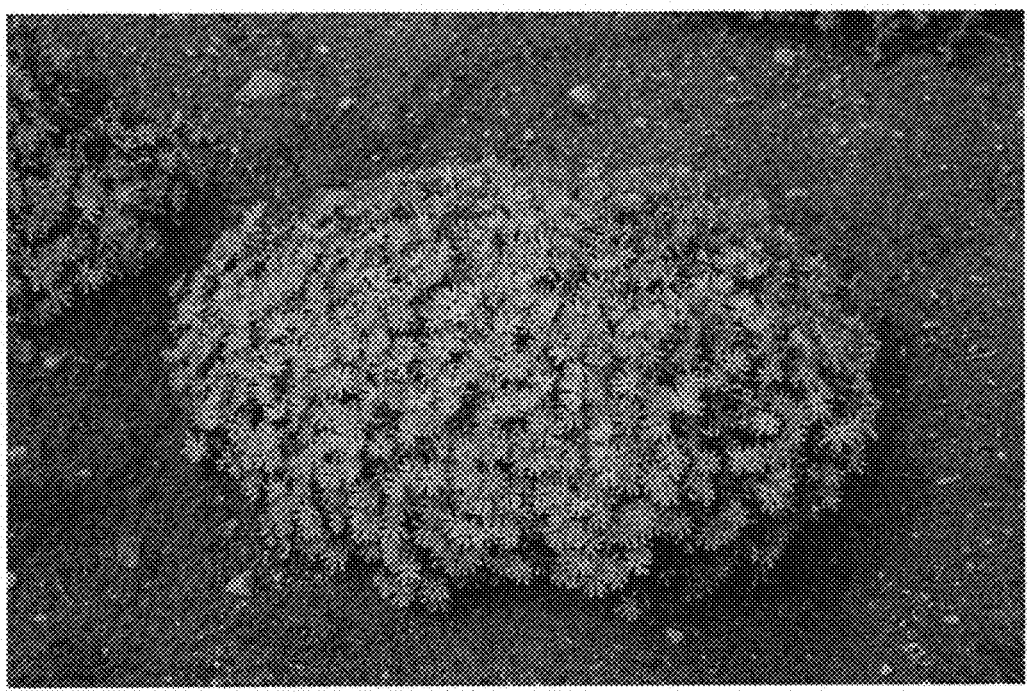
FIG. 1 shows the new plant in peak flower early May.
Figure 2:
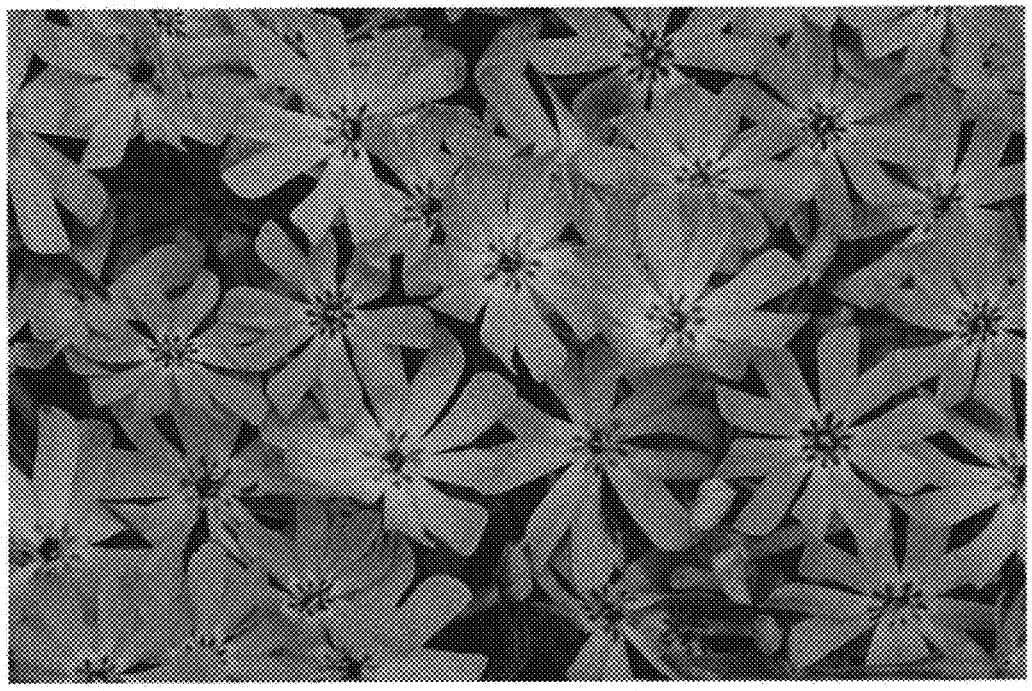
FIG. 2 shows a close-up of the flowers and buds.

The following descriptions and color references are based on the 2015 edition of The Royal Horticultural Society Colour Chart except where common dictionary terms are used. *Phlox* 'Bedazzled Lavender' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid;

Parentage: Female or seed parent is *Phlox subulata* 'Emerald Pink', male or pollen parent is *Phlox bifida* 'Top Notch';

Plant habit: Winter-hardy herbaceous perennial; compact, highly branched; producing about 30 to 40 stiff, highly-branched stems; foliage 10.0 cm tall and 54.0 cm wide; flowering to 15.0 cm tall and 62.0 cm wide;

Propagation: Stem cuttings; rooting in about 10 days;

Time to produce finished crop in 3.8 liter pots: About 8 to 10 weeks; moderately vigorous;

Root: Fibrous and freely branching; color creamy white to tan depending on soil type;

Leaves: Simple; opposite; lanceolate, subulate; apex acute; base truncate, clasping; margin entire with basal one-quarter to whole margin micro-ciliolate; lustrous and glabrous both adaxial and abaxial; about 28.0 mm long by about 3.5 mm wide;

Leaf color: Adaxial and abaxial nearest RHS 137A, with base nearest RHS 157C;

Foliage fragrance: None detected;

Veins: Pinnate; not conspicuous adaxial and abaxial;

Vein color: Same color as surround leaf;

Petiole: Leaves sessile;

Stems: Cylindrical; stiff; strong; upright; covered in leaves distally; about 16.0 mm long and 3.0 mm diameter at base;

Stem color: Variable, nearest RHS 199C and RHS 146D in exposed proximal region;

Nodes: Proximally about 12.0 mm apart; distally less than 1.0 mm apart;

Node color: Same as surrounding stem;

Flowers: Perfect; salverform; cupped; about 22.0 mm across face and cupped to about 8.0 mm deep; with fused corolla tube about 15.0 mm long and 2.0 mm diameter; in branched panicle of about 3 to 5 flowers; attitude upright to outwardly;

Flower longevity: About 5 days on plant; self-cleaning;

Flower fragrance: Pleasantly sweet;

Buds one to two days prior to opening: Narrowly oblanceolate, to narrowly clavate; acute apex with petals implicate; about 21.0 mm long and 2.0 mm diameter in tube and 3.5 mm diameter toward apex;

Bud color: Nearest RHS N87C distally with center portion nearest RHS 86A and tube nearest RHS 85A;

Petals: Five; glabrous; cleft blade and fused claw; blades not imbricate; apex bifid to 6.0 mm deep and lobes separated about 5.0 mm at apex; blade about 9.0 mm long and 2.0 mm wide before tube; lobes about 13.0 mm wide near apex; base fused into a tube about 15.0 mm diameter and 2.0 cm long;

Petal color:

*Adaxial blade*.—Between RHS N78C and RHS N78D with veins nearest RHS N78B, 2.0 mm central eye nearest RHS NN 155D with each petal having two spots about 1.0 mm long of blend between RHS N79B and RHS 79B; central eye of about 5.0 mm diameter nearest RHS 155D, remainder of petal outside of center eye of nearest RHS 84B; main blade lightening to nearest RHS 76C in maturity.

*Abaxial blade*.—Nearest RHS N81D.

*Inner corolla tube*.—Nearest RHS 85A lightening to nearest RHS 145C in basal 2.0 mm.

*Outer corolla tube*.—Nearest RHS 85A and lightening to lighter than RHS 145D at base.

Androecium:

*Filaments*.—Usually five, adnate to inner corolla at various heights; about 1.0 mm and 0.1 mm in diameter; color nearest RHS NN155D.

*Anther*.—Oblong elliptic; dorsifixed; oblong, about 2.0 mm long by 0.7 mm wide; color nearest RHS 17B.

*Pollen*.—Nearly microscopic, spherical; color nearest RHS 23A.

Gynoecium: One pistil per flower; 13.0 mm long;

*Style*.—Cylindrical; about 11.0 mm long and 0.2 mm diameter when flower is mature; color nearest RHS 157D.

*Stigma*.—Trifid in proximal 1.0 mm, about 0.2 mm diameter; persistent after flower abscission; nearest RHS 1C.

*Ovary*.—Inferior; globose; about 1.0 mm long and 1.0 mm diameter; color nearest RHS 144A.

Calyx: Campanulate; about 9.0 mm long and 3.5 mm across at apex;

Sepals: Five; linear; glabrous; acute apex, fused in basal 4.0 mm; margin entire, ciliate; pubescent abaxial, glabrous and lustrous adaxial; individually about 9.0 mm long and 1.0 mm wide at fusion;

Sepal color: Adaxial nearest RHS 137B and abaxial nearest RHS 137C with light blush of nearest RHS N186C;

Peduncle: Finely puberulent; stiff, flexible; upright, cylindrical; about 1.5 mm diameter at base and 3.0 cm long;

Peduncle color: Nearest RHS N77A;

Pedicle: Cylindrical; finely puberulent; flexible; upright to outwardly; to about 10.0 mm long and 1.0 mm diameter;

Pedicle color: Nearest RHS N77A;

Fruit and seeds: Not yet been observed;

Hardiness and culture: The new plant grows best in full sun with plenty of moisture and adequate drainage and can tolerate drier conditions once established; hardy to at least from USDA zone 4 through 8.

Disease and pest resistance: *Phlox* 'Bedazzled Lavender' demonstrates excellent powdery mildew resistance under conditions that would normally show symptoms. Resistance or susceptibility beyond that common of other Hybrid Spring *Phlox* is not known.

I claim:

1. A new and distinct cultivar of *Phlox* plant named 'Bedazzled Lavender', as herein described and illustrated.

* * * * *